US009046508B1

(12) United States Patent
Genovese et al.

(10) Patent No.: US 9,046,508 B1
(45) Date of Patent: Jun. 2, 2015

(54) SIMULATED EXPLOSIVE COMPOSITION

(71) Applicant: U.S. Army Research Development and Engineering Command, APG, MD (US)

(72) Inventors: James A. Genovese, Street, MD (US); Amee W. LaBonte, Havre de Grace, MD (US); Joseph A Domanico, Bel Air, MD (US); Michael F. Kauzlarich, Edgewood, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 90 days.

(21) Appl. No.: 13/804,531

(22) Filed: Mar. 14, 2013

(51) Int. Cl.
*G01N 33/22* (2006.01)
*G01N 33/00* (2006.01)

(52) U.S. Cl.
CPC .............. *G01N 33/227* (2013.01); *G01N 33/22* (2013.01); *Y10T 436/10* (2015.01); *Y10T 436/00* (2015.01)

(58) Field of Classification Search
CPC ............ G01N 33/0037; G01N 33/182; G01N 31/005; G01N 31/227; G01N 21/766
USPC .................................................... 436/110, 106
See application file for complete search history.

(56) References Cited

U.S. PATENT DOCUMENTS

2014/0065030 A1\* 3/2014 Genovese et al. ............. 422/402

\* cited by examiner

*Primary Examiner* — Christine T Mui
(74) *Attorney, Agent, or Firm* — Ulysses John Biffoni

(57) ABSTRACT

The present invention can be characterized as a trainer kit for a Colorimetric Reconnaissance Explosive Squad Screening ("CRESS") kit, which contains a control compound and a set of simulated explosive compositions ("SEC"). The control compound contains no explosive precursor, while each SEC is a combination of one or more explosive precursors that is to be detected by CRESS, and at least one non-explosive additive that reduces the kinetics of the explosive precursor. The SEC retains the colorimetric characteristics of the explosive precursor, but is stable in heat and non-hazardous.

20 Claims, 4 Drawing Sheets

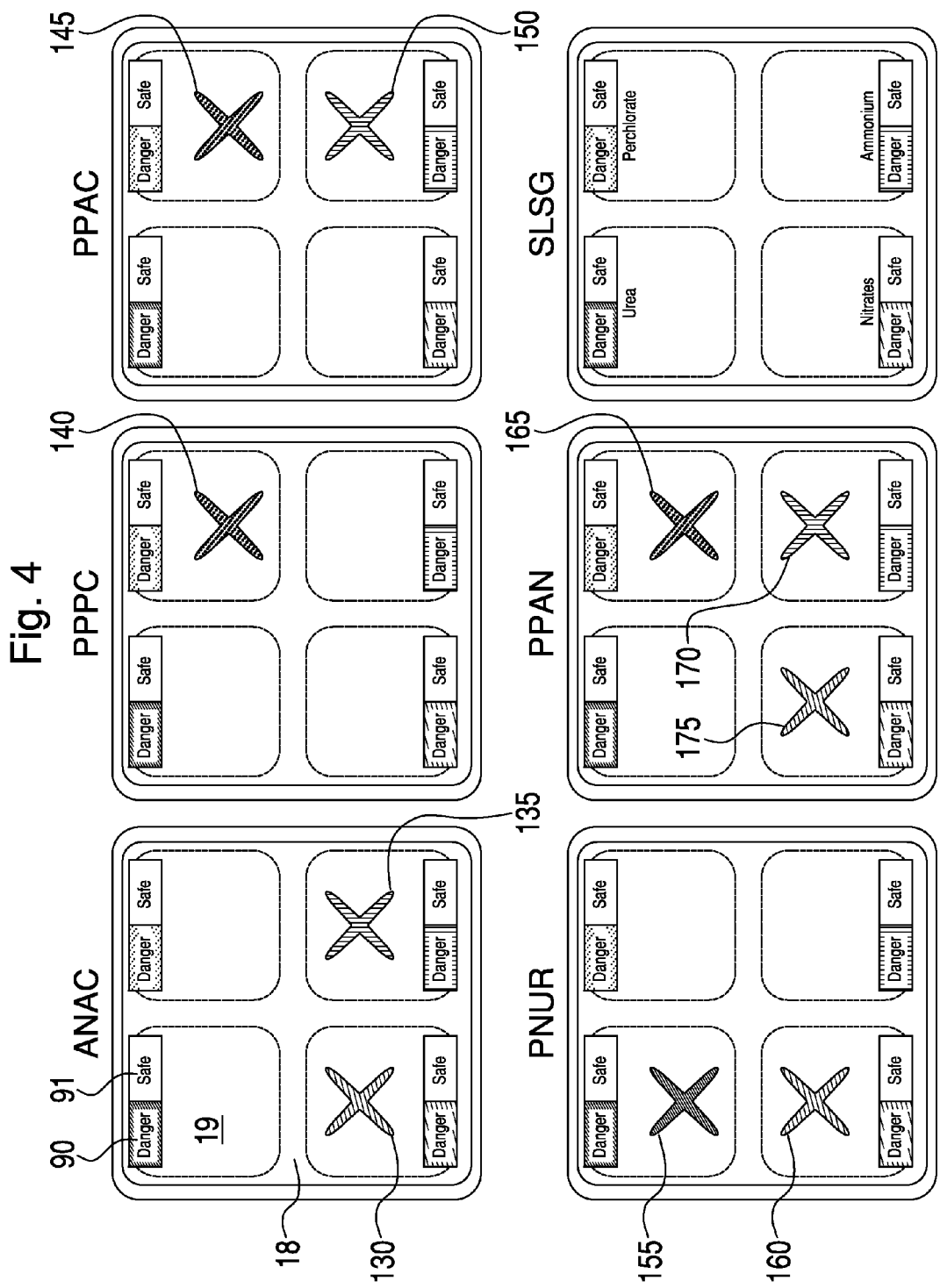

SIMULATED EXPLOSIVE COMPOSITION

GOVERNMENT INTEREST

The invention described herein may be manufactured, used, and licensed by or for the United States Government.

FIELD OF INVENTION

The present invention relates to a testing kit comprising at least one simulated explosive composition ("SEC") that is non-hazardous, wherein the SEC interacts with at least one colorimetric reagent to simulate the color response of its explosive counterpart.

BACKGROUND

Most portable sample detectors only identify one analyte for a given singular device. These analyte detections often rely upon the users ability to select the correct device for a specific analyte. During sampling, users may not be fully knowledgeable of all of the analytes that can possibly be present in the environment. This situation can lead to longer detection times and prolonged durations in a hazardous environment, which may cause severe injuries or death. Additionally, low volatility and/or solid phase analytes (i.e. ammonium nitrate, perchlorate salts, urea, and urea nitrate) do not produce enough vaporous mass due to their inherently low volatilities and, thus, cannot be detected via traditional selective vapor phase sampling means (i.e., ICAM and JCAD).

Given this, a Colorimetric Homemade Explosive Detector ("CHED") or colorimetric reconnaissance Explosive Squad Screening ("CRESS") kit has been developed for this purpose. It is a collection/concentration sampler and detector of liquid or solid phase analytes from diverse environmental matrixes, specifically explosive compounds (or their precursors). Briefly, one uses the sampler component of the CRESS kit to pick up a solid or liquid sample from a surface, which is then folded over the detector component. The CRESS kit further includes colorimetric reagent-containing ampoules located above the sampler component. The user breaks the ampoules to allow the reagent to dissolve the sample and to be absorbed into a swatch of absorbent paper within the detector component. The resultant colors are developed on the paper and are visible through transparent windows, each of which contains an integrated color chart to indicate positive and negative colors.

However, in order to assess the degree of hazard from an unknown substance collected from the environment, users of the CRESS kit need to be trained to interpret the combination of colors from the different visualization windows in CRESS. It is unsafe to use the real hazardous chemicals to produce color changes for training purposes. Therefore, there remains a need for harmless simulated explosive compositions, such that they require minimal or no manipulations to produce the color response of their hazardous counterparts within the CRESS kit.

SUMMARY OF THE INVENTION

The present invention can be characterized as a trainer kit for CRESS, comprising a set of simulated explosive compositions ("SEC"). Each SEC is a combination of at least one real explosive precursor that is to be detected by CRESS, and at least one non-explosive additive that reduces the combustion kinetics of the explosive precursor. The SEC retains the calorimetric characteristics of its explosive component, but is stable in heat and non-hazardous. The trainee can quickly train him or herself by sampling the SEC with a CRESS kit, using the CRESS kit to obtain a calorimetric response from the SEC sample, then interpreting the color change in relation to the potential presence of explosive precursors.

BRIEF DESCRIPTION OF THE DRAWINGS

For a fuller understanding of the nature and advantages of the present invention, one should refer to the details below in conjunction with the accompanying drawings.

FIG. 4 illustrates the visualization media and backside of CRESS from FIG. 3, wherein labels designate the absence or presence of a specific analyte on the visualization media. Six different detected results from six different SECs are shown.

DETAILED DESCRIPTION OF THE INVENTION

The present invention is directed toward a simulated explosive composition ("SEC") kit, comprising a plurality of SEC, and its use within a colorimetric reconnaissance Explosive Squad Screening ("CRESS") kit, wherein each SEC is non-hazardous and has the same color response as its explosive counterpart within the CRESS kit.

CRESS Kit

Figure 1:
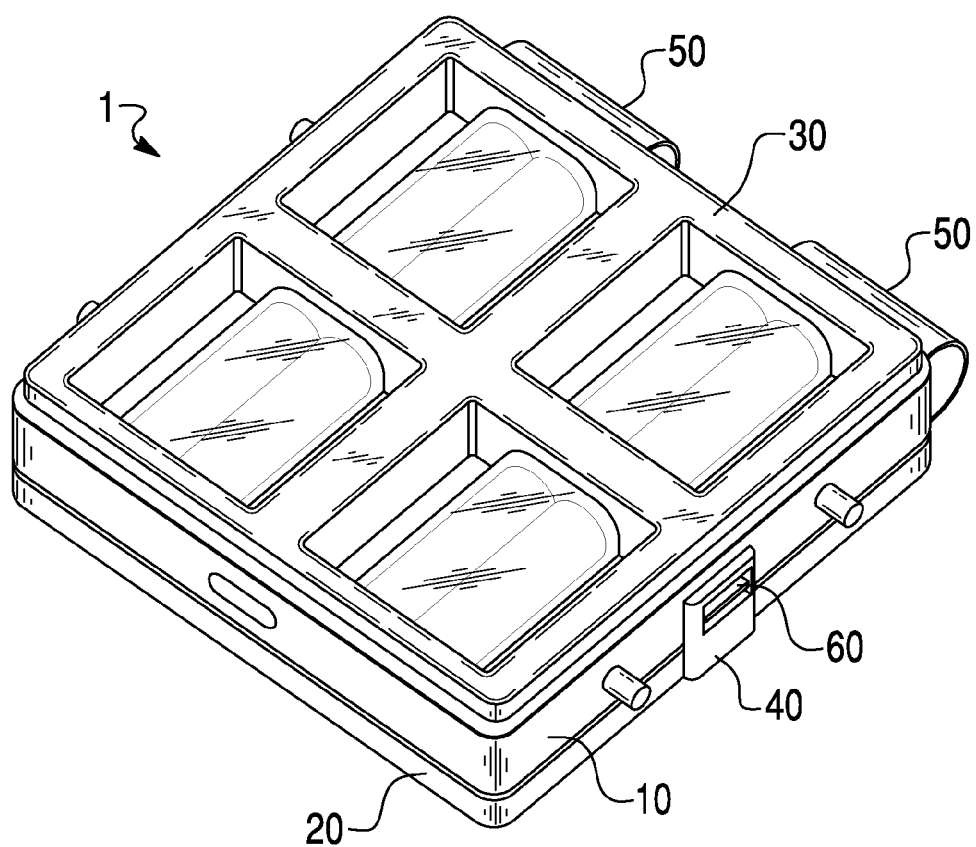
FIG. 1 is a perspective view of a fastened or closed CRESS that has a detection and visualization unit ("DAVU") at the bottom, which is adjacent to and clipped onto a sampling and chemical unit ("SACU") on the top.
Figure 2:
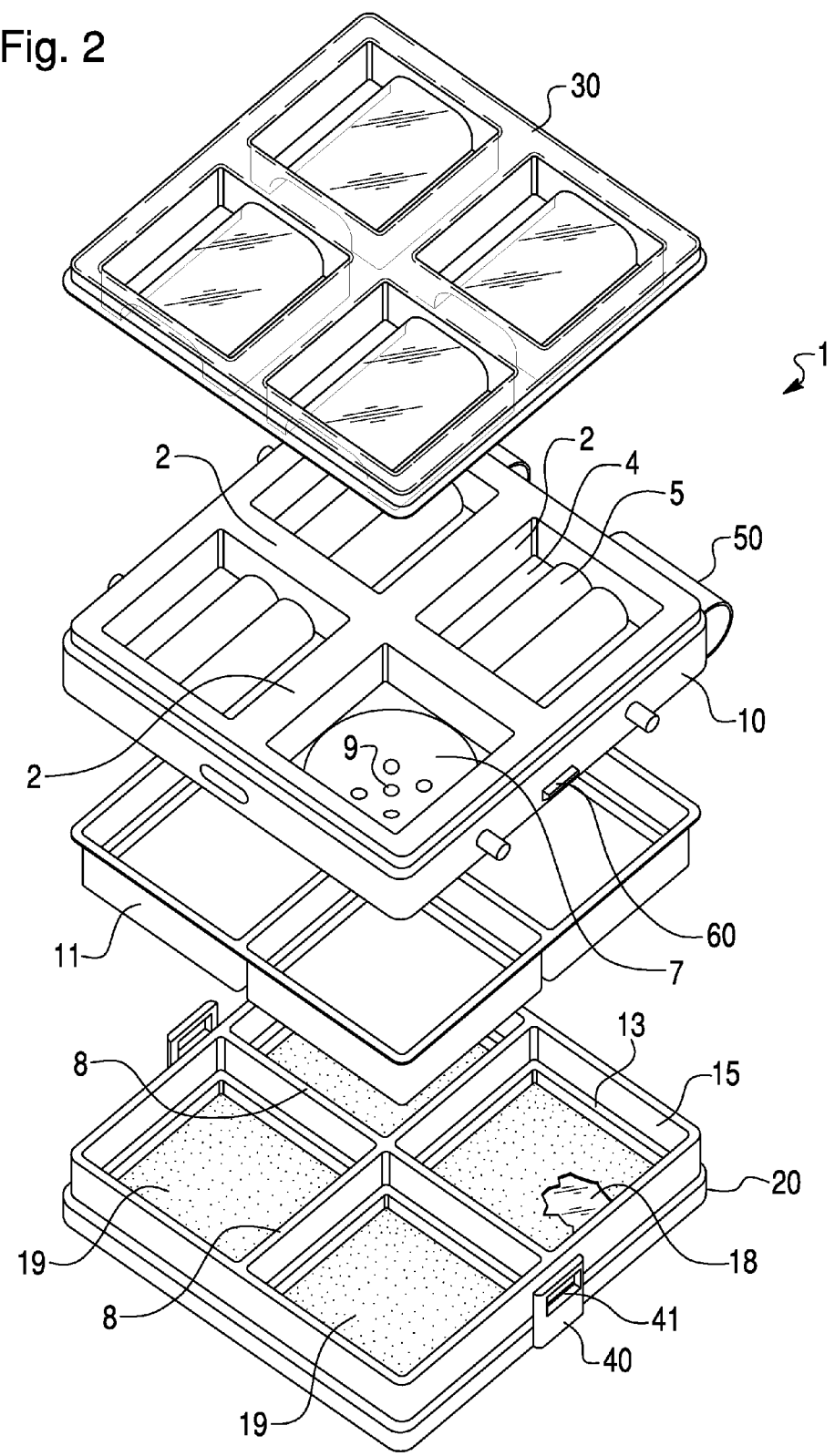
FIG. 2 is an exploded view of the components of the colorimetric detection kit from FIG. 1, wherein the bottom component is the DAVU that is comprised of detection and visualization cells ("DAVC"), and the top component is the SACU comprised of chemical reagent cells "CRC" and a sample collector.

Briefly, the CRESS kit collects multiple samples and detects liquid or solid analytes from these samples, which are obtained from diverse environmental matrixes, or in the present invention, from the testing vials of the SEC kit. As shown in FIGS. 1 and 2, the CRESS kit 1 is comprised of a detection and visualization unit ("DAVU") 20, a sampling and chemical unit ("SACU") 10, and a protective cover 30 that overlays the SACU 10. A sample collector or collection pad 11 is attached to and is part of the SACU. An attachment means is created by affixing clips 40 to groove 41 on the side of unit 20, which receives protrusion 60 that extends from the side of unit 10 that fastens the SACU 10 to the DAVU 20. The SACU 10 can be placed adjacent to and flush against the DAVU 20 to create a tight seal.

Figure 3:
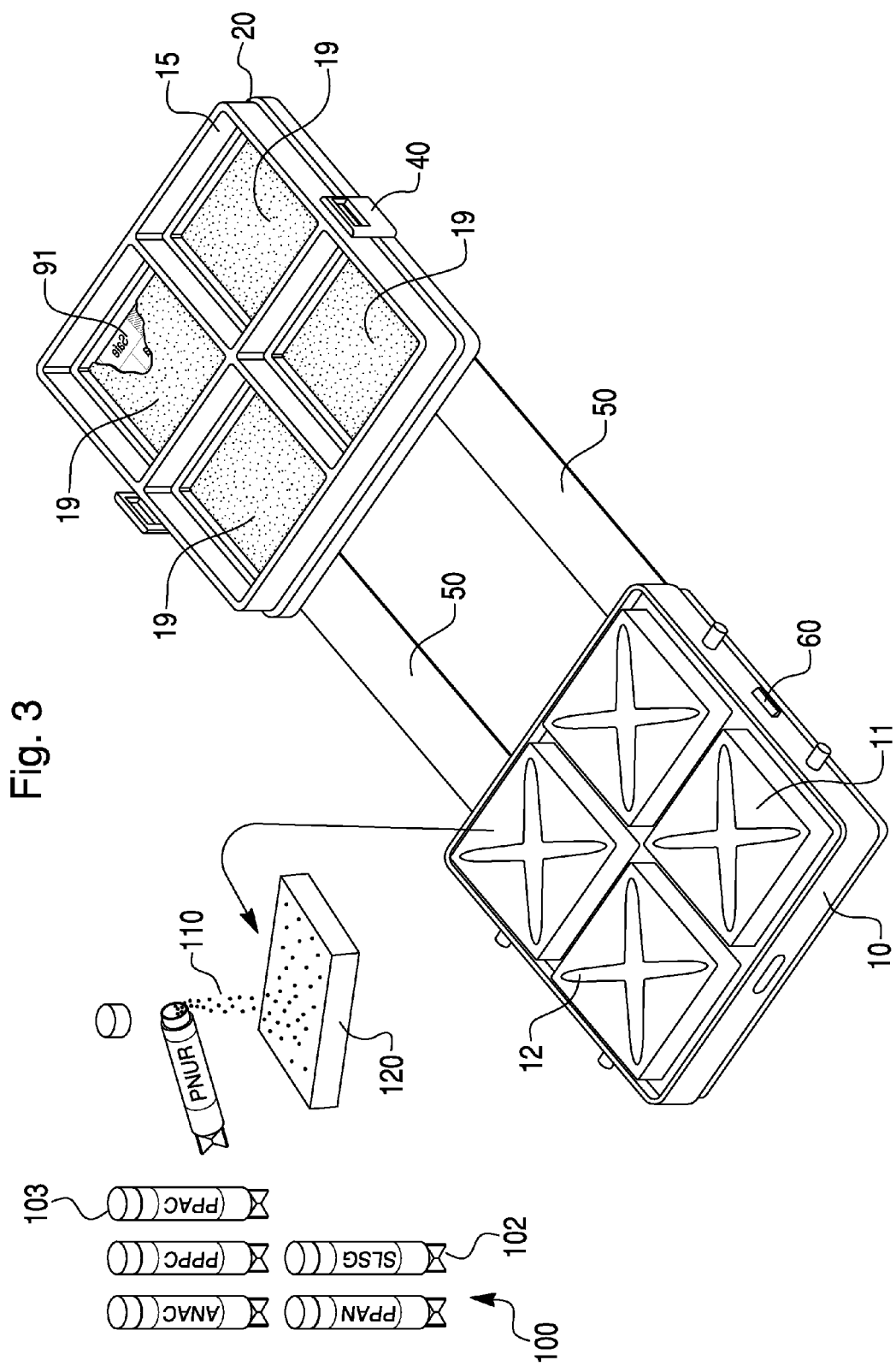
FIG. 3 illustrates a perspective view of an unfastened version of the colorimetric detection kit from FIG. 1, wherein the SACU is separated from the DAVU and ready for the collection of samples. The figure further illustrates a view of vials that contains SEC, wherein one vial is open to release some SEC onto a surface, and the SACU is ready to be placed onto the surface to collect a sample of the released SEC.

The SACU 10 can be separated from the DAVU 20 and remains attached thereto via a pair of flexible hinges 50, allowing the opening and closing of the SACU 10 to the DAVU 20, FIGS. 1, 2, and 3. The bias in hinges 50 tightly seals the SACU 10 to the DAVU 20 to prevent any leakage of chemicals and provides for accurate reactions to take place in each visualization cell. The SACU 10 is comprised of multiple individually confined and equally sized colorimetric reagent cells ("CRC") 4. Each of the CRC 4 houses at least one colorimetric reagent, carried in containers such as breakable ampoules 5. Below ampoules 5 is a directing sink 7, with apertures 9 that enable the colorimetric reagents to be released downward from the broken ampoules 5 to the sampling collector 11 and to DAVU 20. Beneath each of the sinks 7 is placed sample collector surface and pad 11. FIG. 3 illustrates sample collector 11, with a customized surface geometry to concentrate the samples collected and reagents in the form of a pattern. This pattern allows any positive detection to be readily visible by the user on the surface of the visualization media 19 of the DAVU 20, through transparent bottom surface 18.

The DAVU is comprised of multiple individually confined and equally sized detection and visualization cells ("DAVC") 15. Each of the DAVC 15 contains a visualization media 19. The visualization media 19 is comprised of a flat absorbent pad. The absorbent pad can be transparent, white, or of any color that produces a stark contrast with the color change induced by the presence of an analyte. The absorbent pad can be in the form of a filter paper, a silica gel paper, a cloth and a glass fiber disk, etc. The paper or cloth can, for example, be made of cotton yarn, cellulose fibers, rayon blend, borosilicate glass fiber with PVA binder, cellulose and synthetic blend with PVA binder, or cotton linter. The pad may or may not be coated with a sticky adhesive material or other support additives as needed, i.e., impregnated with an enzyme specific for urea hydrolysis. The preferred materials are cotton linter that is commercially available as Whatman® Absorbent Sinks, and cloth membrane that is commercially available as Dupont™ Sonatra® 8426. Additionally, the visualization media 19 may also be the sampling or collection pad, which collects samples from the environment. The reacted calorimetric reagents from SACU are absorbed by the visualization media 19, in each of the DAVC 15. The visualization media then indicates the color change in the presence of a specific analyte, or for the present invention, an explosive precursor. The visualization media 19 is viewable through transparent bottom surface 18 of DAVU 20.

Furthermore, the SACU 10 has partitions 2 to separate each of the CRC 4. The underside of partitions 2 are formed as interlocking channels or grooves (not shown). In a fastened or closed position, the grooves fit snuggly onto the partitions 8 that divide each of the corresponding detection and visualization cells ("DAVC") 15, in DAVU 20, in order to create a tight seal to prevent leakage of chemical reagents and samples from one CRC 4 to another.

The explosives that can be detected via the CRESS kit are selected from nitrate explosives, perchlorate explosives, azide explosives, HMTD (hexamethylennetriperoxidediamine), picrate explosives, TATP (triacetonetriperoxide), and mixtures thereof. For example, the CRESS kit as described above can be designed to detect the precursors of nitrate and perchlorate explosives. Fuel and oxidizers are the two required components for producing these explosives. Nitrate explosive is comprised of nitrates as the oxidizer and urea as the fuel. Meanwhile, perchlorate explosive mixture is comprised of perchlorate as the oxidizer and ammonium as the fuel. In a preferred embodiment of the CRESS kit as shown in FIGS. 3 and 4, four quadrants of the detection window are available to detect the four explosive precursors (nitrates, urea, perchlorate and ammonium) via the color changes. The CRESS kit detection color scheme is shown below in Table 1:

TABLE 1

| Analyte | Colorimetric reagent from ampoules | Negative | Positive |
| --- | --- | --- | --- |
| Ammonium | Nessler's Test | White | Brown |
| Perchlorate | Methlene Blue Test | Blue | Purple |

TABLE 1-continued

| Analyte | Colorimetric reagent from ampoules | Negative | Positive |
| --- | --- | --- | --- |
| Urea | Urease (Enzyme) Test | Orange-Yellow | Pink/Red |
| Nitrate | Diphenyl-Amine Oxidation | White | Black |

For urea detection, the enzyme urease is impregnated onto the reaction substrate of the CRESS kit to hydrolyze urea. The hydrolysis reaction subsequently increases the pH of the substrate. This pH change induces a color change of the colorimetric reagent methyl red from light yellow to pink. For perchlorate detection, the ion pairing methylene blue impregnated onto the reaction substrate will be dissolved by DI water and form a colored precipitate with perchlorates, changing from blue to purple. For nitrate detection, diphenyl amine in a strong acid (phosphoric acid) forms a dissolvable salt that will produce a very dark (black) oxidation colorimetric response in the presence of nitrates, which can also be used to confirm the presence of urea nitrate when used in conjunction with the urea test. The last test is for ammonium ion and the CRESS kit uses the premade Nessler's reagent that results in a yellow/orange/brown (concentration dependent) color change in the presence of $NH_3$ as it reacts with the mercury in the reagent.

The CRESS kit color detection layout is depicted in FIG. 4, wherein four detection windows (quadrants) are present such that each precursor occupies one detection window. As shown in FIG. 4, window 122 detects urea, window 124 detects perchlorate, window 126 detects nitrate, and window 128 detects ammonium.

SEC Kit

A SEC kit is comprised of a plurality of SEC, each of which is a combination of a real explosive or explosive precursor to be detected by a CRESS kit, and a non-explosive additive that reduces the kinetics of the explosive or explosive precursor. The SEC retains the colorimetric characteristics of its explosive or explosive precursor component, but is stable in heat and non-hazardous. The SEC kit includes: 1) one control vial that contains a non-SEC compound and induces no color change and 2) approximately 1 to 10 vials of SEC. Preferably, the SEC kit includes one control vial and approximately 1 to 8 vials of SEC, and more preferably one control vial and approximately 1 to 6 vials of SEC. Each vial contains an equal amount of the various substances aforementioned. The SEC kit further includes a manual that instructs the user on how to use the kit in accordance with the CRESS kit, and how to interpret the colored results from the CRESS kit.

As shown in FIG. 3, the SEC kit 100 includes one control vial 102 and five SEC vials 103, which are labeled respectively as "SLSG", "ANAC", "PPPC", "PPAC", "PNUR", and "PPAN". The SEC kit 100 also includes an information sheet as shown in Table 1 about the SEC, which lists a four-digit code that represents the test results for each vial. Each of the four digits represents a quadrant or DAVC 15, which indicates the presence of an explosive precursor or the lack thereof by color changes. The order of the digits corresponds to known explosive precursors in the following sequence: perchlorate, nitrate, ammonium and urea. Each of the four-digit test result code consists of 1's and/or 0's to indicate the expected outcome, wherein a positive color response in a designated DAVC 15 is designated as 1, and a negative color response is designated as 0. For example, a test result of "0110" indicates that the SEC tested positive for nitrate and ammonium, and negative for perchlorate and urea. These labels and test result codes are developed to help provide trainees with an "unknown" material while still allowing the trainer to determine the accuracy of the trainee's interpretation of the colored responses from the CRESS kit. To further ensure the identification of the training compound, the SEC kit 100 is packaged into colored capsules, each containing about one gram of material. Table 2 lists examples of labels for each SEC, its test result code, capsule color, and components:

TABLE 2

| Label | Test Result | Capsule Color | Component One | Component Two |
|---|---|---|---|---|
| ANAC | 0011 | Yellow | Ammonium nitrate | Ammonium chloride |
| PPPC | 0100 | Blue | Potassium perchlorate | Potassium chloride |
| PPAC | 0101 | Red | Potassium perchlorate | Ammonium chloride |
| PNUR | 1010 | Purple | Potassium nitrate | Urea |
| PPAN | 0111 | Orange | Potassium perchlorate | Ammonium nitrate |
| SLSG | 0000 | White | Soda Lime silica glass | N/A |

It must be noted that in other examples of the SEC kit 100, more SEC vials and their corresponding combinations of test results are also useful. For instance, a test result code of "0100" is possible with a SEC that is a combination of potassium nitrate and potassium chloride.

Referring to Table 2, when chemicals from the Component One column are mixed thoroughly with the chemicals listed in the Component Two column, the non-explosive additives within these two types of chemicals change the reaction rates of the explosive precursors. The non-explosive additives also function as a heat sink to reduce the combustion kinetic of the explosive precursors. Without wishing to be bound by theory, the reduction is caused by the colligative effects of mixing a contaminant with a neat material. The non-explosive additives are the non-explosive anions or cations of compounds in Components One and Two, or compounds that do not result in an explosive mix when they are being added to make the SEC. Examples of non-explosive additives are anions selected from chloride, bromide, oxide and fluoride; and cations selected from sodium, potassium, ammonium, copper, iron, magnesium, calcium and aluminum.

Each SEC has a ratio of the explosive precursor to the non-explosive additives in the range of 1:10 to 10:1, preferably 1:5 to 5:1. Alternatively, each SEC contains at least one explosive precursor in the amount of 1 to 90 wt. %, preferably 10 to 80 wt. %, and more preferably 20 to 70 wt. %, balanced by the non-explosive additives.

Method of Use

The trainee can be safely trained to detect potential explosives by 1) sampling different SEC with a CRESS kit; 2) using the CRESS kit to obtain a colorimetric response from each SEC; and 3) interpreting the combinations of color change to assess the presence of explosives.

As shown in FIG. 3, for colorimetric detections from a SEC, a pre-weighted vial of SEC kit 100 labeled as "PNUR" is opened and SEC 110 is poured onto surface 120. The CRESS kit 1 is unfastened and the collection pad 11 of all four quadrants, correspond to four CRC 4 on the bottom of SAVU 10 is pressed against the suspect surface 120. The kit is then fastened and the calorimetric reagents within each of the CRC 4 are released from their containers 5 and directed downward onto the collection pad 11 for reaction with any suspect analyte or explosive precursor, and the reacted calorimetric reagent is then directed onto and into the visualization media 19. The reacted calorimetric reagents are absorbed by the visualization media 19, in each of the DAVC 15. As shown in FIG. 4, the visualization media 19 subsequently indicates a color change (a color that corresponds to "Danger") in the presence of a specific analyte or explosive precursor. The visualization media 19 is viewable through the transparent bottom surface 18 of DAVU 20.

EXAMPLE

All of the SEC that are listed in Table 2 were tested to verify their status as non-hazardous. Specifically, each SEC was subjected to differential scanning calorimetry ("DSC") and burn testing. For the DSC testing, approximately 2.5 mg of each of the SEC was placed into a DSC Q100 by TA Instruments, and heated from ambient to 550° C. The instrument recorded the heat flow verses temperature. None of the SEC exploded.

For the burn test, the SEC samples were placed in a v-block with a specific length and heated with a torch at one end. The rate at which the samples burned down the length of the block was to be calculated. However, none of the SEC burned when exposed to the torch.

Each of the SEC was then tested with a CRESS kit to verify their designated color results. Each of the SEC was poured from its storage vial onto a separate testing surface, and each SEC was tested separately with a new and unused CRESS kit, wherein the unused and opened CRESS kit was pressed against the testing surface to collect the SEC. Each CRESS kit was then used according to the operating instruction as mentioned hereinabove. Every SEC produced colorimetric response that was identical to their explosive precursors. FIG. 4 illustrates the test results of the labeled SEC from Table 2, wherein "ANAC" tested positive for nitrates 130 and ammonium 135; "PPPC" tested positive for only perchlorate 140; "PPAC" tested positive for perchlorate 145 and ammonium 150; "PNUR" tested positive for urea 155 and nitrate 160; "PPAN" tested positive for perchlorate 165, nitrates 175 and ammonium 170; and "SLSG" was control substance that tested negative for all precursors.

It must be noted that the SEC that were labeled as "PPAC", "PNUR" and "PPAN" were all tested by the CRESS kit to contain explosives (nitrate/urea and perchlorate/ammonium), yet none had posed any danger during the testing.

The testing kit of the present invention provides advantages over prior art testing devices, in that the entire colorimetric explosive detection process stays the same for the SEC as its hazardous counterpart. No specially engineered system is required. The only component that changes is the composition of the targeted explosive analytes. In this invention special non-explosive additives are added to reduce sensitivity and combustion of the explosive precursor.

Also, packing and production of the SEC kit is improved because potential hazardous events have been significantly reduced. Department of Transportation issues dealing with explosive hazards are also significantly reduced due to a large reduction in pyrotechnic sensitivity.

The invention claimed is:

1. A simulated explosive composition ("SEC") kit for safely training users to detect explosives, comprising: a control compound and a plurality of simulated explosive compositions, wherein said control compound contains no explosive precursor, and said simulated explosive compositions are each comprised of a combination of one or more explosive precursors, and at least one non-explosive additive that reduces combustion kinetics of said explosive precursors, wherein said simulated explosive compositions interact with colorimetric reagents to simulate the colored responses of said explosive precursors.

2. The SEC kit of claim 1, wherein said explosive precursor is selected from the group consisting of urea, potassium perchlorate, ammonium nitrate, potassium nitrate, and mixtures thereof.

3. The SEC kit of claim 1, wherein said non-explosive additive is selected from anions comprising chloride, bromide, oxide and fluoride; and cations comprising sodium, potassium, ammonium, copper, iron, magnesium, calcium and aluminum.

4. The SEC kit of claim 1, wherein said simulated explosive compositions are comprised of said explosive precursor in the amount of 10 to 80 wt. %, balanced by said non-explosive additive.

5. The SEC kit of claim 4, wherein said simulated explosive compositions are comprised of said explosive precursor in the amount of 20 to 70 wt. %, balanced by said non-explosive additive.

6. The SEC kit of claim 1, wherein said simulated explosive compositions have a ratio of said explosive precursor to said non-explosive additive in the range of 1:10 to 10:1.

7. The SEC kit of claim 6, wherein said simulated explosive compositions have a ratio of said explosive precursor to said non-explosive additive in the range of 1:5 to 5:1.

8. The SEC kit of claim 1, wherein said colorimetric reagents detect at least one fuel and at least one oxidizer.

9. The SEC kit of claim 8, wherein said colorimetric reagent is selected from the group consisting of methyl red, methylene blue, diphenyl amine and phosphoric acid and Nessler's reagent.

10. The SEC kit of claim 8, wherein said fuels are urea and ammonium and said oxidizers are nitrates and perchlorate.

11. A method for safely training users to detect potential explosives, comprising:
(a) spreading a simulated explosive composition of claim 1 onto a surface;
(b) collecting said simulated explosive composition onto a colorimetric explosive detector, which comprises:
  (i) a sampling and chemical unit ("SACU") separate from and placeable adjacent to and juxtaposed against a detection and visualization unit ("DAVU") and containing at least one colorimetric reagent reactive with said simulated explosive compositions of claim 1;
  (ii) said DAVU containing a visualization surface for receiving said reacted colorimetric reagent; and
  (iii) a sample collector placed so as to be capable of receiving said colorimetric reagents and juxtaposed to said visualization surface when said SACU is placed against said DAVU; and
(c) obtaining a colored response from said DAVU of said detector, wherein at least one positive colored response indicates the presence of at least one explosive precursor.

12. The method of claim 11, wherein said explosive precursor is selected from urea, potassium perchlorate, ammonium nitrate, potassium nitrate, and mixtures thereof.

13. The method of claim 11, wherein said simulated explosive composition is comprised of said explosive precursor in the amount of 10 to 80 wt. balanced by said non-explosive additive.

14. The method of claim 13, wherein said simulated explosive composition is comprised of said explosive precursor in the amount of 20 to 70 wt. %, balanced by said non-explosive additive.

15. The method of claim 11, wherein said simulated explosive composition has a ratio of said explosive precursor to said non-explosive additive in the range of 1:10 to 10:1.

16. The method of claim 11, wherein said colorimetric reagents detect at least one fuel and at least one oxidizer.

17. The method of claim 11, wherein said colorimetric reagent is selected from methyl red, methylene blue, diphenyl amine and phosphoric acid and Nessler's reagent.

18. The method of claim 16, wherein said fuels are urea and ammonium and said oxidizers are nitrates and perchlorate.

19. The method of claim 16, wherein said colored detection of at least one said fuel in combination with at least one said oxidizer indicates at least one potential explosive.

20. The method of claim 19, wherein said explosive is selected from nitrate explosives and perchlorate explosives.

* * * * *